(12) United States Patent
Karp et al.

(10) Patent No.: US 12,121,656 B2
(45) Date of Patent: Oct. 22, 2024

(54) ACCESSORY FOR REMOVING AND SEQUESTERING WASTE ANESTHETIC GAS

(71) Applicant: Thomas Jefferson University, Philadelphia, PA (US)

(72) Inventors: Alice Jane Karp, Philadelphia, PA (US); Delara Kiani, Philadelphia, PA (US); Cary Hess, Philadelphia, PA (US); Corey Jameson, Philadelphia, PA (US)

(73) Assignee: Thomas Jefferson University, Philadelphia, PA (US)

( * ) Notice: Subject to any disclaimer, the term of this patent is extended or adjusted under 35 U.S.C. 154(b) by 626 days.

(21) Appl. No.: 17/072,674

(22) Filed: Oct. 16, 2020

(65) Prior Publication Data

US 2021/0113789 A1 Apr. 22, 2021

Related U.S. Application Data

(60) Provisional application No. 62/915,724, filed on Oct. 16, 2019.

(51) Int. Cl.
| | | |
|---|---|---|
| *A61M 16/00* | (2006.01) | |
| *A61M 1/00* | (2006.01) | |
| *A61M 16/01* | (2006.01) | |
| *A61M 16/06* | (2006.01) | |
| *A61M 16/08* | (2006.01) | |

(52) U.S. Cl.
CPC .......... *A61M 16/009* (2013.01); *A61M 1/784* (2021.05); *A61M 1/86* (2021.05); *A61M 16/06* (2013.01); *A61M 16/0816* (2013.01); *A61M 2202/0241* (2013.01)

(58) Field of Classification Search
CPC ............ A61M 16/009; A61M 16/0093; A61M 16/06–0694; A61M 2202/0241; A61M 16/0605; A61M 16/0616; A61M 16/0622; A61M 16/0816; A61M 16/0003; A61M 1/784; A61M 1/86; A61M 16/01; A61M 16/104; A61M 2207/00; A61B 5/082
See application file for complete search history.

(56) References Cited

U.S. PATENT DOCUMENTS 4,248,218 A * 2/1981 Fischer ............... A61M 16/009
128/207.18
4,807,617 A 2/1989 Nesti
(Continued)

FOREIGN PATENT DOCUMENTS

| CN | 204601327 U | 9/2015 | |
|---|---|---|---|
| CN | 106693141 A * | 5/2017 | ............ A61M 16/06 |

(Continued)

OTHER PUBLICATIONS

Machine Translation of CN204601327U accessed on Feb. 22, 2023 (Year: 2023).*

(Continued)

*Primary Examiner* — Kendra D Carter
*Assistant Examiner* — Mautin I Ashimiu
(74) *Attorney, Agent, or Firm* — Riverside Law LLP

(57) ABSTRACT

The present invention provides plastic and rubber devices molded to fit on existing anesthesia masks. The devices capture and sequester waste anesthetic gases that escape out of the perimeter of an anesthesia mask that has been fitted onto a patient.

9 Claims, 2 Drawing Sheets

(56) References Cited

U.S. PATENT DOCUMENTS

| | | | |
|---|---|---|---|
| 6,263,874 B1 * | 7/2001 | LeDez | ............... A61M 16/085 128/205.25 |
| 2009/0235932 A1 | 9/2009 | Nashed | |
| 2010/0122706 A1 | 5/2010 | Moenning, Jr. | |

FOREIGN PATENT DOCUMENTS

| | | | | |
|---|---|---|---|---|
| WO | WO-8201999 A1 * | 6/1982 | ............ | A61M 16/06 |
| WO | WO-8806044 A1 * | 8/1988 | ............ | A61M 16/06 |
| WO | WO-2014178730 A2 * | 11/2014 | ............ | A61M 16/01 |

OTHER PUBLICATIONS

Machine Translation of CN106693141A Abstract accessed on Mar. 3, 2023 (Year: 2023).*
Friembichler et al. "A scavenging double mask to reduce workplace contamination during mask induction of inhalation anesthesia in dogs", Acta Veterinaria Scandinavica, vol. 53:1, (2011).
Retrieved from https://airmedical.es/en/anesthesiamasks/ on Jan. 3, 2022, Airmedical Products, Medicvent.

* cited by examiner

ACCESSORY FOR REMOVING AND SEQUESTERING WASTE ANESTHETIC GAS

CROSS-REFERENCE TO RELATED APPLICATIONS

This application claims priority to U.S. Provisional Patent Application No. 62/915,724, filed Oct. 16, 2019, the contents of which are each incorporated by reference in its entirety.

BACKGROUND OF THE INVENTION

Current methods deliver anesthesia to a patient via an anesthesia mask, a simple, flexible, disposable plastic structure shaped to complement a human face. An inflatable cuff on the mask comes in direct contact with the patient's face, in theory creating a relatively tight seal between mask and skin. Aerosolized anesthetic, flowing from an anesthesia machine, is piped into the mask where it is inhaled by the patient and once the patient is rendered unconscious, mechanically forced into the patient's respiratory system. The initial phase of anesthesia delivery is referred to as "induction"; a patient is "induced" from a conscious, waking state to an unconscious, paralyzed, and pain-insensitive state. Following induction, the anesthesia mask is removed from the patient's face and an endotracheal intubation device is placed, securing access to the patient's airway. Endotracheal tubes used in the delivery of anesthesia often have an inflatable cuff which is pumped to inflation in the patient's airway, creating a seal to block the flow of gases either into or out of the patient's airway, leaving the endotracheal tube as the only avenue by which gas exchange occurs.

Potent inhaled anesthetics (PIAs) include halothane, sevoflurane, desflurane, and isoflurane. All PIAs, to one degree or another, pose hazards to human health. PIAs are associated with reproductive toxicity, spontaneous miscarriages in pregnant persons as well as an increased risk of congenital abnormalities in offspring. In other words, PIAs are thought to be both abortifacients as well as teratogens. PIAs are also associated with hepatotoxicity, neurotoxicity, cognitive impairment, as well as increased incidence of malignancy. Within the field of anesthesia pregnant women are already barred from environments in which PIA exposure may occur. Increasingly, data demonstrate that not only are pregnant persons or people desiring to become pregnant at risk, but partners of those chronically exposed to PIAS may be at risk as well, despite no first-hand exposure.

Unintentional exposure to PIAS is a serious occupational hazard faced by personnel in the operating room, both in hospitals and in outpatient settings. Nurse anesthetists and anesthesiologists are typically exposed to the highest atmospheric concentrations of PIAS. PIA leaks are most likely to occur during the induction phase of anesthesia delivery, often occurring due to poor mask seal or failure to turn off PIA gas flow when the anesthesia mask is removed from the patient's face prior to intubation. Patients with beards, edentulous patients, and patients with other atypical face shapes or structures further increase the likelihood of poor mask seal and escape of PIAS into the room air. These escaped PIAS are then referred to as waste anesthetic gases (WAGs).

Thus, there is a need in the art for devices that mitigate waste anesthetic gas release. The present invention meets this need.

SUMMARY OF THE INVENTION

In one aspect, the present invention relates to a gas sequestration device, comprising: a toroidal inner frame; an outer skirt attached to the inner frame; a plurality of inlet ports or ducts positioned within the inner frame; and at least one evacuation port positioned on the outer skirt, each evacuation port being fluidly connected to the plurality of inlet ports or ducts.

In one embodiment, the device is sized to wrap around an outer perimeter of an anesthesia mask. In one embodiment, the inner frame is rigid or semi-rigid. In one embodiment, the skirt is constructed from a flexible material. In one embodiment, the at least one evacuation port comprises a connector selected from the group consisting of: luer locks, fir tree connectors, stepped connectors, threaded connectors, and flanged connectors. In one embodiment, the fluid connection supports a vacuum.

In one aspect, the present invention relates to a method of sequestering waste anesthetic gas, the method comprising the steps of: providing the gas sequestration device of the present invention; attaching the device to a complementary anesthesia mask, such that at least one gap is formed between the device and the mask; connecting each of the evacuation ports to a vacuum source; and applying a vacuum to each of the evacuation ports, such that the at least one gap is depressurized to create circumferential suction around the mask.

In one embodiment, the vacuum source is an anesthesia machine. In one embodiment, the step of applying a vacuum suctions waste anesthetic gas from around the mask into the plurality of inlet ports or ducts and out of the at least one evacuation port.

BRIEF DESCRIPTION OF THE DRAWINGS

The following detailed description of exemplary embodiments of the invention will be better understood when read in conjunction with the appended drawings. It should be understood, however, that the invention is not limited to the precise arrangements and instrumentalities of the embodiments shown in the drawings.

DETAILED DESCRIPTION

The present invention provides plastic and rubber devices molded to fit on existing anesthesia masks. The devices capture and sequester waste anesthetic gases that escape out of the perimeter of an anesthesia mask that has been fitted onto a patient.

Definitions

It is to be understood that the figures and descriptions of the present invention have been simplified to illustrate elements that are relevant for a clear understanding of the present invention, while eliminating, for the purpose of clarity, many other elements typically found in the art. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined elsewhere, all technical and scientific terms used herein have the same meaning as commonly understood by one of ordinary skill in the art to which this invention belongs. Although any methods and materials similar or equivalent to those described herein can be used in the practice or testing of the present invention, the exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6, and any whole and partial increments there between. This applies regardless of the breadth of the range.

Figure 1:
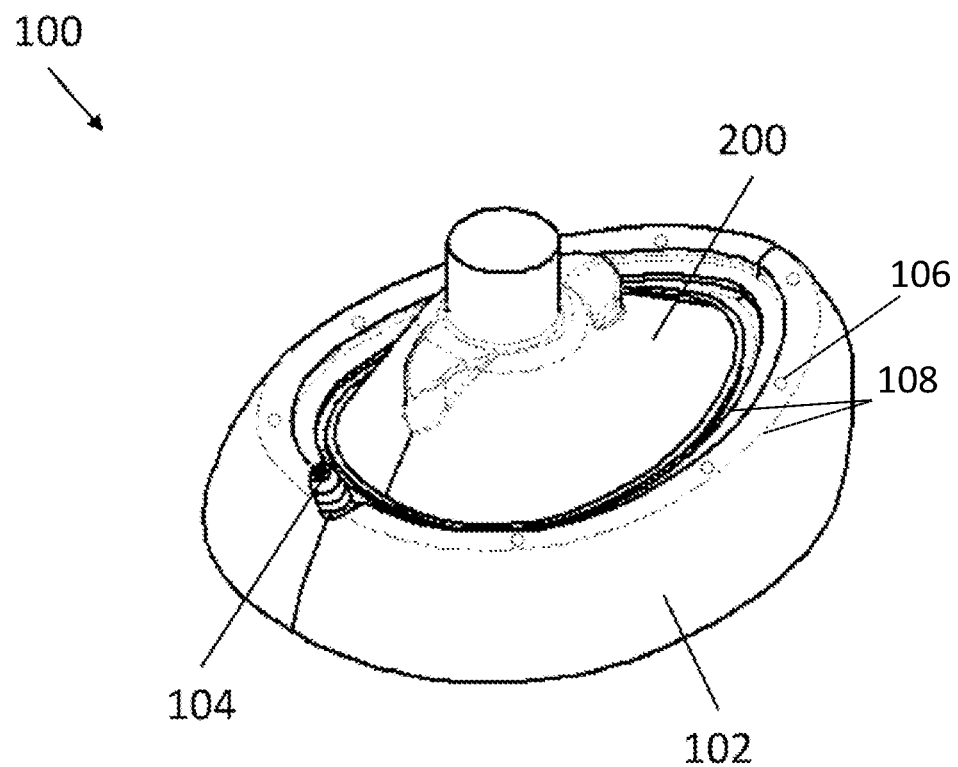
FIG. 1 depicts a perspective view of an exemplary gas sequestration device attached to an anesthesia mask.
Figure 2:
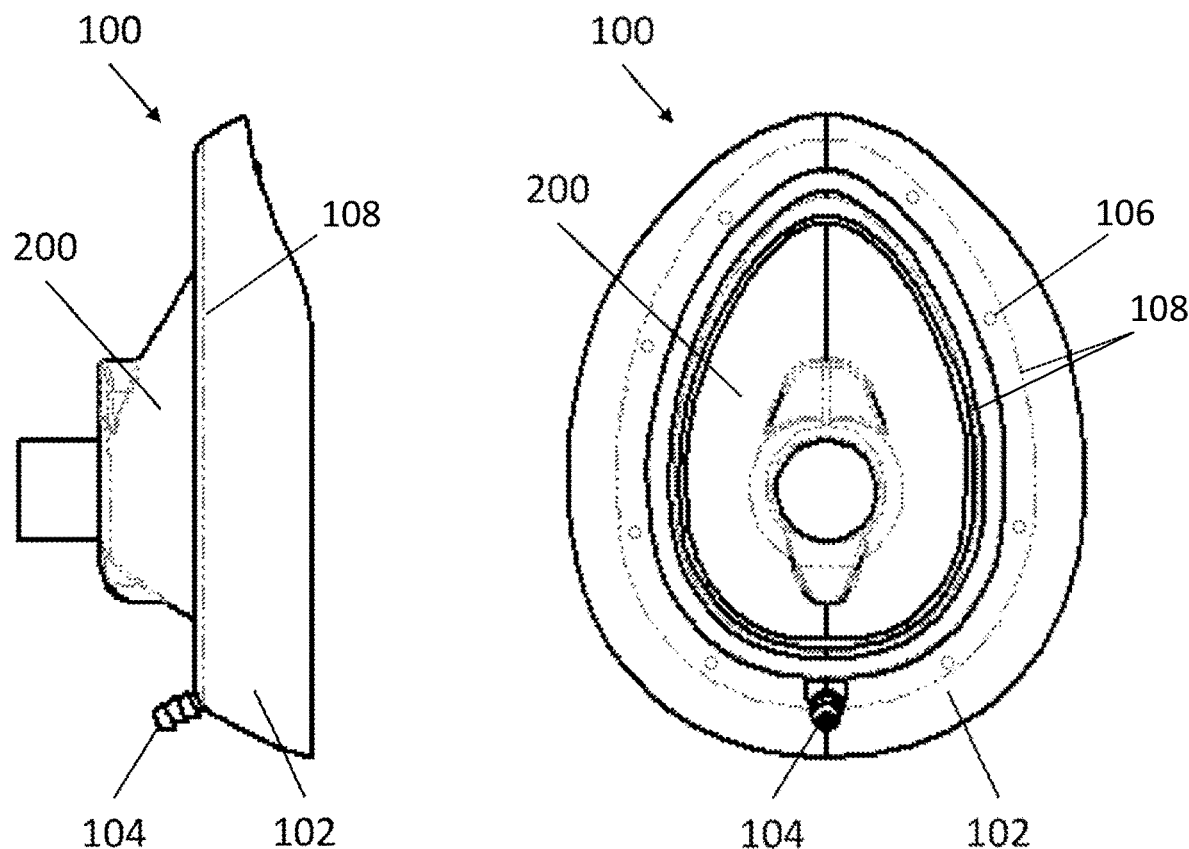
FIG. 2 depicts a side view (left) and front view (right) of an exemplary gas sequestration device attached to an anesthesia mask.

Referring now to FIG. 1 and FIG. 2, an exemplary gas sequestration device 100 is depicted. Device 100 comprises a flexible skirt 102 that wraps circumferentially around an outer perimeter of an anesthesia mask 200. In some embodiments, skirt 102 extends to the level of an inflatable cuff of mask 200. Device 100 further comprises an inner frame 108 that supports skirt 102 on its exterior and a plurality of inlet ports 106 or ducts on its interior (not pictured). Device 100 can have any desired number of inlet ports 106 or ducts arranged in any suitable manner. The inner frame 108 can be rigid or semi-rigid and can have any desired shape that substantially conforms to a perimeter of an anesthesia mask, such as a circular toroid or an ovoid toroid. Skirt 102, being joined to the inner frame 108, deforms under hand pressure to facilitate effective hand-to-mask placement. Skirt 102 further comprises at least one evacuation port 104 on its exterior, wherein the at least one evacuation port 104 is fluidly connected to the plurality of inlet ports 106 or ducts on the interior of the inner frame 108. In this manner, fluids that are evacuated by the plurality of inlet ports 106 or ducts are removed through the at least one evacuation port 104. The at least one port 104 can include any commonly used quick connect/disconnect connectors, including but not limited to luer locks, fir tree connectors, stepped connectors, threaded connectors, flanged connectors, and the like. In some embodiments, device 100 comprises a single monolithic construction. In some embodiments, device 100 comprises a multi-component construction, wherein two or more sub-components are assembled to form device 100.

The present invention also provides methods of sequestering waste anesthetic gas. Anesthesia machines commonly used in the art have built-in suction apparatuses used to remove secretions, vomit, or other potential obstructions from a patient's airway. These suction systems have a plurality of suction ports to which accessory lines may be attached. The methods thereby begin with a first step, wherein a gas sequestration device is provided and attached to a complementary anesthesia mask. In a second step, each of the ports is connected to an anesthesia machine or other vacuum source by a suction line. The vacuum source can optionally include one or more filters, such as a carbon filter. In a third step, a vacuum is applied to the at least one port, which depressurizes any gaps between the gas sequestration device and the mask to creating circumferential suction around the mask. The negative pressure gradient between the gas sequestration device and the surrounding atmosphere pulls escaping gas (including waste anesthetic gas) into the gaps, whereupon the waste gas is suctioned into the plurality of inlet ports or ducts, out of the at least one port, and into a connected vacuum source. From there, the waste gas can be ejected into a remote location or exhausted into an air handling system that receives anesthesia gas from the anesthesia flow "loop." In some embodiments, the gas sequestration devices can be used as a passive seal in the absence of a vacuum source. Placing a gas sequestration device around an anesthesia mask can minimize or even block excess waste gas from escaping around an anesthesia mask.

The present invention also provides methods of sequestering airborne particles. Subjects wearing a mask in any situation, including but not limited to receiving anesthesia or supplementary oxygen, may carry one or more contagions such that infectious droplets and aerosols exiting from the nose or mouth may escape from the periphery of a mask and be dispersed to the surrounding environment. The gas sequestration devices can be provided in the absence of a vacuum source to form an enhanced physical barrier around a mask to block airborne droplets and aerosols. The gas sequestration devices can also be connected to a vacuum source to isolate airborne droplets and aerosols.

In some embodiments, the gas sequestration devices can be made in a universal size. In some embodiments, the gas sequestration devices can be scaled smaller or larger to fit users having smaller and larger faces or to fit anesthetic masks having smaller or larger sizes. In some embodiments, the gas sequestration devices are disposable and/or recyclable. In some embodiments, the gas sequestration devices are sterilizable and reusable, such as by autoclaving or wiping down with a disinfectant.

Components of the gas sequestration devices of the present invention can be constructed from any suitable material, including but not limited to metals and polymers, such as stainless steel, titanium, aluminum, polyether ether ketone (PEEK), polyethylenes, polyvinyls, polyurethanes, polyamides, polycarbonates, silicones, and the like. In some embodiments, certain components or portions of certain components can be constructed from a transparent or translucent material. Transparent or translucent materials can permit unobstructed visual inspection of the device and patient during use. The components and systems can be made using any suitable method known in the art. The method of making may vary depending on the materials used. For example, devices substantially comprising a metal may be milled from a larger block of metal or may be cast from molten metal. Likewise, components substantially comprising a plastic or polymer may be milled from a larger block, cast, or injection molded. In some embodiments, the devices may be made using 3D printing or other additive manufacturing techniques commonly used in the art.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A gas sequestration device, comprising:
    a toroidal inner frame;
    an outer skirt attached to the toroidal inner frame;
    a plurality of inlet ports or ducts positioned within the inner frame; and
    at least one evacuation port positioned on the outer skirt, each evacuation port being fluidly connected to the plurality of inlet ports or ducts;
    wherein at least one gap in the shape of a circumferential flow loop is formed between the gas sequestration device and an outer perimeter of a mask, wherein the flow loop is separated and spaced apart from both a central mask opening and a central portion of the mask adjacent to the central mask opening, and wherein the at least one gap is configured to create circumferential suction around the outer perimeter of the mask when suction is applied to the plurality of inlet ports.

2. The device of claim 1, wherein the device is sized to circumferentially wrap around an outer perimeter of an anesthesia mask.

3. The device of claim 1, wherein the toroidal inner frame is rigid or semi-rigid.

4. The device of claim 1, wherein the outer skirt is constructed from a flexible material.

5. The device of claim 1, wherein the at least one evacuation port comprises a connector selected from the group consisting of: luer locks, fir tree connectors, stepped connectors, threaded connectors, and flanged connectors.

6. The device of claim 1, wherein the fluid connection supports a vacuum.

7. A method of sequestering waste anesthetic gas, the method comprising the steps of:
    providing the gas sequestration device of claim 1;
    attaching the sequestration device to a complementary anesthesia mask, such that at least one gap is formed between the device and the complementary anesthesia mask;
    connecting each of the evacuation ports to a vacuum source; and
    applying a vacuum to each of the evacuation ports, such that the at least one gap is depressurized to create circumferential suction around the complementary anesthesia mask.

8. The method of claim 7, wherein the vacuum source is an anesthesia machine.

9. The method of claim 7, wherein the step of applying the vacuum suctions waste anesthetic gas from around the complementary anesthesia mask into the plurality of inlet ports or ducts and out of the at least one evacuation port.

* * * * *